United States Patent [19]

Brunke et al.

[11] Patent Number: 4,788,177
[45] Date of Patent: Nov. 29, 1988

[54] USE OF ALKYL ETHERS OF 2,2,2-TRICHLORO-1-PHENYLETHANOL AS ODORIFEROUS SUBSTANCES

[76] Inventors: Ernst-Joachim Brunke, Holbeinstrasse 6; Claus-Hermann Kappey, Schratweq 1, both of 3450 Holzminden, Fed. Rep. of Germany

[21] Appl. No.: 77,806

[22] Filed: Jul. 27, 1987

[30] Foreign Application Priority Data

Jul. 31, 1986 [DE] Fed. Rep. of Germany ....... 3626085

[51] Int. Cl.⁴ .............................................. A61K 7/46
[52] U.S. Cl. ......................................... 512/20; 512/8; 512/25; 568/812
[58] Field of Search ....................... 568/663, 626, 812; 512/20, 8, 25

[56] References Cited

U.S. PATENT DOCUMENTS

| 2,606,213 | 8/1952 | Ladd et al. ........................... 568/663 |
| 4,087,538 | 5/1978 | Portnoff ............................... 424/274 |

FOREIGN PATENT DOCUMENTS

| 283581 | 10/1952 | Switzerland ......................... 568/812 |
| 445638 | 6/1975 | U.S.S.R. ............................... 568/812 |

OTHER PUBLICATIONS

Hurd et al, "J. Amer. Chem. Soc.", vol. 60, pp. 1909–1911 (1938).
Hanby et al, "J. Chem. Soc.", p. 114 (1946).
Kolbezen et al., "J. Amer. Chem. Soc.", vol. 77, pp. 5410–5411 (1955).

*Primary Examiner*—Werren B. Lone

[57] ABSTRACT

It was found that ekylic ethers of 2,2,2-trichloro-1-phenylethanol with the general formula A

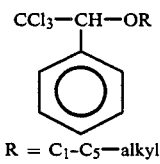

$$CCl_3-CH-OR \quad\quad A$$

$R = C_1\text{-}C_5\text{—alkyl}$ are excellently usable as odoriferous substances, especially as components of perfume oils for cosmetic and technical consumer goods.

1 Claim, No Drawings

USE OF ALKYL ETHERS OF 2,2,2-TRICHLORO-1-PHENYLETHANOL AS ODORIFEROUS SUBSTANCES

It has long been known (Steffen Arctander, "Perfume and Flavor Chemicals", Vol. 2, Montclair, N.J., U.S.A. 1969, Ref. No. 2976-2978)) that carboxylic acid esters of 2,2,2-trichloro-1-phenylethanol, such as 2,2,2-trichloro-1-phenylethyl acetate, propionate and butyrate have olfactory properties can can be used as components of perfume oils. This holds especially for the acetate that has the formula B

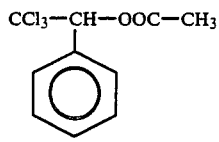

B is relatively simply producible and which according to Arctander is distinguished by a mold balsamic, green-rosy fragrance of good adhesion. These esters, to be sure, are usable only in small amounts, because the fragrance also contains undesired earthy side-notes, which at higher concentrations manifest themselves in a troublesome manner. Furthermore, the stability of these esters is unsatisfactory, especially in use in detergents and similar products with basic milieu.

There exists, therefore, a considerable need for synthetic rose-type odiferous substances which can be produced economically and with constant quality, remain stable in relatively long storage also in contact with other substances, especially in a basic milieu, and have agreeable fragrance notes of sufficient intensity as close as possible to nature, to be able to influence advantageously the fragrance of cosmetic or technical consumer goods.

It was now found that alkyl ethers of 2,2,2-trichloro-1-phenylethanol with the general formula A

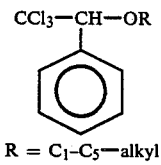

A $R = C_1-C_5-alkyl$ fulfill this demand in a virtually ideal manner, for they are extremely stable compounds, producible without problems, with extremely advantageous olfactory properties. They have, namely, close-to-nature fragrance notes of the general type "flowery-rosy" with spicy side aspects, which combind good adhesion with great irradiation and even in relatively high concentrations contain no troublesome, for example earthy side notes. Furthermore, they are excellently suited as ingredients of perfume oils, especially those of the rose type, as they appreciably reinforce their freshness, adhesion and radiation.

The invention, accordingly, relates to the use of alkyl ethers of 2,2,2-trichloro-1-phenylethanol of the general formula A as odiferous substances, especially as components of perfume oils for cosmetic and technical consumer goods. In particular the formula A there comprises ethers with the following alkyl residues:

R=methyl
R=ethyl
R=propyl or isopropyl
R=butyl or its isomers and
R=amyl (penyl) or its isomers.

Of this group the methyl ether is the preferred compound. Its fragrance has great radiation and has a rosy main note with spicy-woody side aspects which is strongly demanded and very much desired. With the higher ethers, too, a rosy main note is present, but the side aspects shift more in the spicy-herbal direction. Therewith also the higher ethers are very interesting.

The methyl ether has already been described in the literature in other context and without reference to any olfactory properties (Chem. Ber. 110, pp. 96–106 (1977) as well as Angew. Chemie 85, pp. 868–869 (1973)), while the other ethers present new compounds. The advantageous olfactory properties of all these ethers are surprising and differ clearly from those of the carboxylic acid esters of 2,2,2-trichloro-1-phenylethanol mentioned at the outset. nor are they derivable from the olfactory behavior of structurally related compounds, for except for the carboxylic acid esters that have already been in use since the end of the past centry, hitherto in this respect there had still only been investigated the underlying alcohol 2,2,2-trichloro-1-phenylethanol, which does not become to the fundamental type "rose" and has no significance as an odoriferous substance (Arctander, loc. cit., Ref. No. 2975). Aside from this, it also holds generally that the olfactory properties of known odoriferous substances do not admit of any cogent conclusions about the properties of structurally related compounds, because neither the mechanism of odor perception nor the influence of the chemical structure on the odor perception have been adquately investigated, and, accordingly, it cannot be foreseen whether a modified structure of known odoriferous substances leads at all to changes of the olfactory property and whether these changes are positively or negatively assessed.

For the preparation of the alkyl ethers of general formula A it is possible to proceed according to the usual known methods of ether production, for example by conversion of the 2,2,2-trichloro-1-phenylethanol with use of alkyli hydride and the alkyl sulfates, alkyl halides or alkyltosylates corresponding to the residue R, or under phase transfer conditions with alkali hydroxide. (Chem. Ber. 110, loc. cit. as well as Angew. Chemie 85, loc. cit.)

The following examples of use are to explain the invention without restricting it. With "PW" there are designated there in each case parts by weight.

EXAMPLE 1

As point of departure there was used a rose base with the composition:

| | | |
|---|---|---|
| 10 PW | Brahmanol ® | |
| 40 PW | Phenylethyl alcohol | |
| 140 PW | Citronellol | |
| 100 PW | Geraniol/Nerol | |
| 6 PW | Linalool | |
| 4 PW | Farnesol | |
| 4 PW | Aldehyde C-9 (10% in dipropylene glycol) | |
| 8 PW | Phenylacetaldehyde 50% | |
| 5 PW | Citral | |
| 2 PW | (+)—Carvon | |
| 15 PW | Citronellylacetate | |
| 2 PW | Phenylacetic acid methylester | |

-continued

| | |
|---|---|
| 10 PW | Methyeugenol |
| 1 PW | Rose oxide, inactive |
| 3 PW | Isodamascon (10% in dipropylene glycol) |
| 350 PW | |

This rose base consists essentially of the main odiferous substances of rose oil and has a sweet rose harmony. By addition of 150 PW of the methylether according to formula A there arises another composition of the "rose" type, which is distinguished at a relatively high content of 30% by wt of methylether by a natural freshness and great radiation.

EXAMPLE 2

As point of departure there was used a rose base with the composition:

| | |
|---|---|
| 5 PW | Aldehyde C-9 (10% in dipropyleneglycol) |
| 5 PW | Isocyclocitral |
| 5 PW | Isodamascon |
| 10 PW | rose oxide left |
| 10 PW | Eugenol |
| 20 PW | Dimethylbenzylcarbinylacetate |
| 20 PW | Pehnylacetaldehyddimethylacetal |
| 250 PW | Rhodinol |
| 600 PW | Phenylethyl alcohol |

-continued

| |
|---|
| 925 PW |

This rose base is characterized essentially by the relatively high volatility of its rose note. The addition of 75 PW of methylether according to formula A (7.5% by wt of methylether in the resulting perfume oil) leads to a clearly improved adhesion of this scent note and simultaneously reinforces the rose petal aspect in an advantageous manner.

We claim:

1. A process for augmenting or enhancing the aroma of a perfume composition or a cologne comprising the step of adding to a perfume base or a cologne base an aroma augmenting quantity of at least one alkyl ether of 2,2,2-trichloro-1-phenylethanol with the general formula A

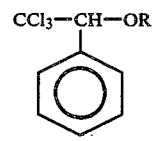

$$CCl_3-CH-OR \qquad A$$

wherein R is an alkyl group having from 1 to 5 carbon atoms.

* * * * *